(12) United States Patent
Wellisz et al.

(10) Patent No.: US 6,511,482 B1
(45) Date of Patent: Jan. 28, 2003

(54) CRANIAL BONE FLAP FIXATION CLIP

(75) Inventors: Tadeusz Z. Wellisz, Los Angeles, CA (US); Eric V. Hohenstein, Los Angeles, CA (US)

(73) Assignee: Bioplate, Inc., Los Angeles, CA (US)

( * ) Notice: Subject to any disclaimer, the term of this patent is extended or adjusted under 35 U.S.C. 154(b) by 240 days.

(21) Appl. No.: 09/669,438

(22) Filed: Sep. 25, 2000

Related U.S. Application Data

(63) Continuation-in-part of application No. 09/435,645, filed on Nov. 9, 1999, now Pat. No. 6,168,596.

(51) Int. Cl.[7] .............................................. A61B 17/80
(52) U.S. Cl. ........................................... 606/69; 606/51
(58) Field of Search .............................. 606/69, 70, 71, 606/151, 75

(56) References Cited

U.S. PATENT DOCUMENTS

| | | |
|---|---|---|
| 4,364,382 A | 12/1982 | Mennen |
| 4,651,724 A | 3/1987 | Berentey et al. |
| 5,201,737 A | 4/1993 | Leibinger et al. |
| 5,474,557 A * | 12/1995 | Mai .............................. 606/75 |
| 5,501,685 A | 3/1996 | Spetzler |
| 5,549,620 A | 8/1996 | Bremer |
| 5,586,985 A | 12/1996 | Putnam et al. |
| 5,669,912 A | 9/1997 | Spetzler |
| 5,718,705 A | 2/1998 | Sammarco |
| 5,797,916 A | 8/1998 | McDowell |
| 5,810,822 A | 9/1998 | Mortier |
| 5,849,012 A * | 12/1998 | Abboudi ....................... 606/69 |
| 5,916,217 A | 6/1999 | Manthrop et al. |
| 5,961,519 A | 10/1999 | Bruce et al. |

FOREIGN PATENT DOCUMENTS

SU        1816443 A1    12/1990

* cited by examiner

*Primary Examiner*—Todd E. Manahan
(74) *Attorney, Agent, or Firm*—William W. Haefliger

(57) ABSTRACT

A clip to inter-connect primary and secondary bone zones having edges, comprising in combination a tab to extend over a surface or surfaces of at least one of the bone zones, above a level defined by the one surface; a first projection carried by the tab and having a hook to engage a bone zone at its edge, and below the level. The projection may be bowed, and may have S-configuration.

23 Claims, 5 Drawing Sheets

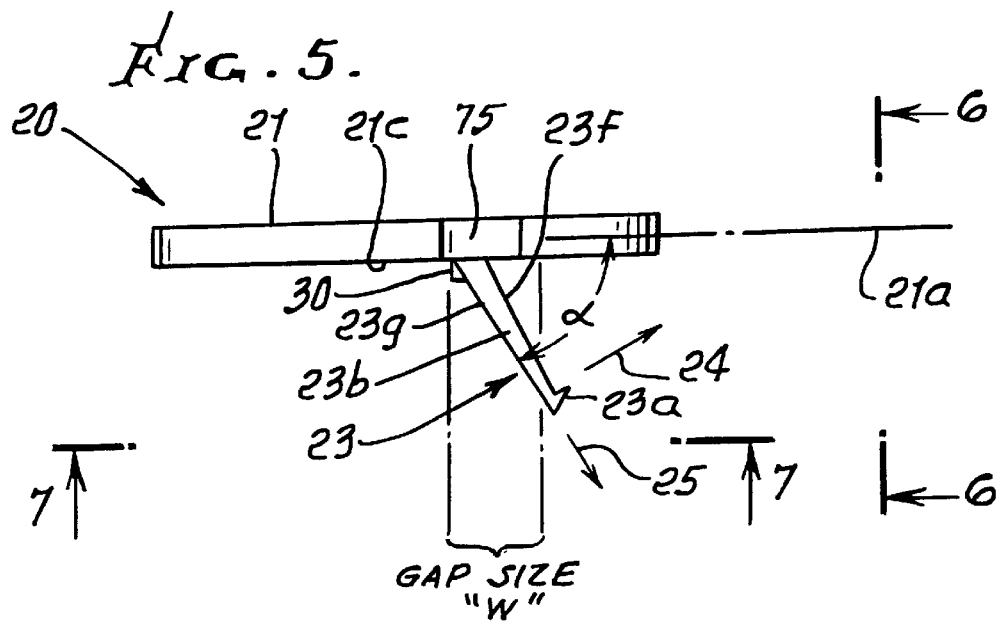
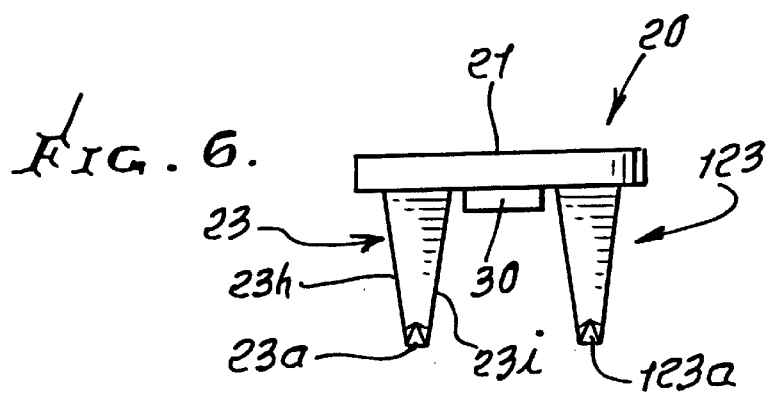
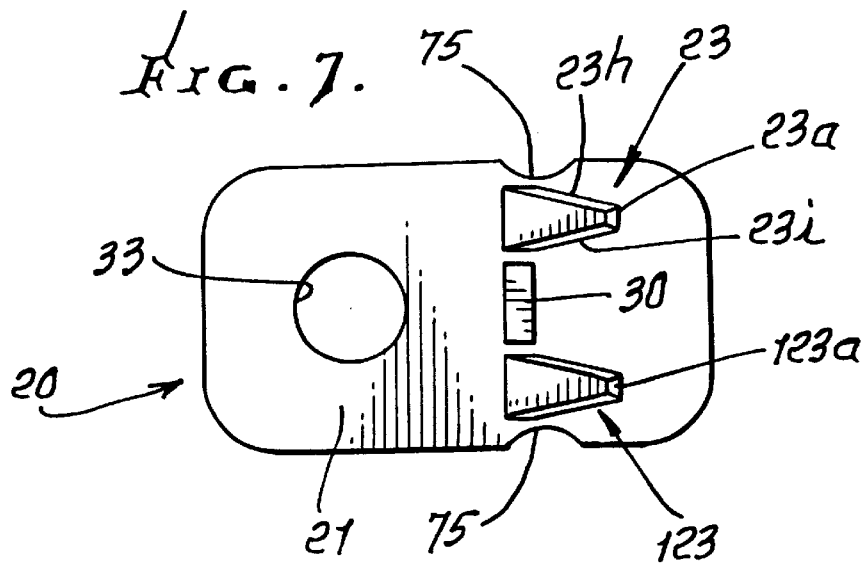

CRANIAL BONE FLAP FIXATION CLIP

This application is a continuation-in-part of Ser. No. 09/435,645, filed Nov. 9, 1999, now U.S. Pat. No. 6,168,596.

BACKGROUND OF THE INVENTION

This invention relates generally to the alignment and fixation of bone segments as required for appropriate bone healing, for example after fracture or surgical intervention, and specifically to a device, and the tools needed to install the said device, for the alignment and fixation of cranial bone fragments.

In cases of bone fragmentation where bone fixation is desired, the appropriate alignment of the bone is also a desired result. This is especially true in the cranium, where bone fragmentation can occur as a result of trauma, congenital deformity, or of surgical intervention. In the field of neurosurgery, cranial bone fragments are frequently cut and removed to create defects to allow for access into the cranial cavity and the brain.

The bony cranium is generally regarded to have two surfaces: the outer surface which is characterized by the outer cortex of the bone and is adjacent to the scalp and soft tissue; and the inner surface which is characterized by the inner cortex of the bone and which is adjacent to the cranial cavity and the brain. Between the inner cortex and the outer cortex, which are dense layers of bone, lies the medullary layer which generally consists of soft bone and bone marrow. When a bone fragment is created, a cut between the bone fragment (the primary bone zone) and the remainder of the cranium (the secondary bone zone) is present.

Several methods of alignment and fixation of primary and secondary bone zones are known. Traditional techniques involve the use of several pieces of filament, such as wire, that are tied after being threaded through holes drilled obliquely through the outer cortex to the cut surface of both bone zones. Precise alignment of the two zones can be difficult and the technique can be cumbersome.

Commonly, the zones of bone can be aligned and fixated with a system of plates and screws (U.S. Pat. Nos.: 5,372, 598; 5,413,577; and 5,578,036). A plate made of metal or other substance can be fixated to the outer cortex of the primary bone zone with screws whose penetration of the bone can be limited to the outer cortex. With three of more plates attached to the primary bone in such a way that the plates protrude beyond the edges of the primary bone zone, the primary bone zone can be introduced into a defect and aligned to the outer cortex of the secondary bone zone without danger of the primary bone zone falling too deeply into the defect in the secondary bone zone and exerting pressure on the underlying tissue such as the brain. Fixation can then be achieved by employing additional screws fixating the plates to the outer cortex of the secondary bone zone. Plates and screws systems are believed to be the only devices currently in use that allow for the alignment and fixation of the zones, while preventing the primary bone zone from falling below the level of the secondary bone zone without actually introducing a component of the device below the secondary bone zone. Plate and screw systems can be expensive and time consuming to use.

Devices that align the two bone zones by way of compressing them between the two disks positioned along the inner and outer cortex have been described. (Foreign Patents: DE 19603887C2, DE 19634699C1, DE 29812988U1, EP 0787466A1). A pin connects the two disks aligning and securing two bone zones. These devices introduce foreign material that is left below the inner cortex, and they do not protect the underlying tissue from compression during the installation procedure.

Devices that fixate bone zones using friction forces created by a cam without a component that extends below the inner cortex are known and described (Patent DE 19634697C1). These devices also do not protect the brain from compression during the installation procedure.

Intramedulary pins are well known in the orthopedic fields for alignment of long bones. Such pins have also been described for cranial fixation; however, the bone zones can not be aligned in three dimensions with this technique.

There is a need for an alignment and fixation device that is simple and rapid to use, versatile, and ultimately cost effective.

OBJECTS OF THE INVENTION

An important object of the invention is to provide a device and instruments for its use that aligns the one cortex of a primary zone with one cortex of a secondary bone zone without extending to the opposing cortex, and which fixates the bone zones to each other. When used in the field of neurosurgery, the device is applied to the primary bone zone and it aligns the outer cortex of the primary bone zone with the outer cortex of the secondary body zone; it prevents the primary bone zone from entering the cranial cavity; and it provides fixation of the two bone zones. The alignment feature can be used independently from the fixation feature. An example of the use of the alignment feature is in the replacement of a cranial bone fragment which will be held in place by the tissue forces of the scalp, which allows for the bone fragment to be elevated away from the cranial cavity in cases where brain swelling occurs. Fixation can also be applied to attach the alignment device to the bone, using elements alone or in combination such as filaments, screws, rivets, pins, clips, cams, friction or adhesives. The alignment aspect of the invention can also be applied to situations where it is desired to offset the alignment of the bone fragment to the adjacent bone such as where the object is to create a more prominent chin by cutting the bone of the chin and advancing the bone fragment.

The fixation feature of the invention is likewise independent from the alignment feature. The fixation feature of the device relies on the principle that the device is fixated to the primary bone zone and the fixation feature grips the secondary bone zone by means of spring loaded tab or hook elements engaging the soft areas of the medullary space, irregularities along the cut surface, or a slot cut into the cut surface of the secondary bone zone.

SUMMARY OF THE INVENTION

The invention provides an improved clip, and method of its use, meeting the above need or needs.

As will be seen, the preferred clip is configured to interconnect primary and secondary bone zones having edges spaced apart by a gap, the clip comprising a) a tab to extend over a surface or surfaces of at least one of said bone zones, above a level defined by the one surface, and b) a first projection carried by the tab and having a hook to engage a bone zone at its edge, and below a portion of the tab that extends over the projection.

As will be seen, the projection typically extends angularly downwardly from the tab at angle between 50° and 60° from a plane defined by the tab, and terminates at the hook, and the hook has a sharp terminal to enable penetration of bone marrow. The projection has a shank configured to provide enhanced bending resilience in a direction toward the hook. The shank is desirably bowed, and may have two sections, at least one of which is bowed. In this regard, the sections preferably form an S-shaped configuration, as will be seen. The tab may contain a through hole to receive a fastener that fastens to one of the bone zones; and the tab may be elongated to bridge portions of both the primary and secondary bone zones.

It is another object to provide a clip configuration incorporating a second projection carried by the tab and having a hook to engage the primary bone zone at its edge, and below said front level. Further, the two projections may advantageously extend in generally parallel relation, and angularly downwardly from the tab, and terminate at said hooks, whereby bending forces generated by deflection of both projections are utilized to achieve enhanced holding by the two hooks to the same edge of the bone zone. The preferred S-shape of the projection serves to enhance such holding.

Yet another object is to provide a tab retraction notch, or two retraction notches proximate the ends of the projections closest to the tab; and an alignment protrusion may be provided to be integral with the tab and located between the first and second projections for engagement with an edge of one bone zone. Also, one of the bone zones may typically comprise a bone flap removed from a cranium.

An additional object is to provide an improved method for attaching primary and secondary bone zones having edges, the method including the steps:

a) providing a tab to extend over a surface or surfaces of at least one of said bone zones, above a level defined by the one surface, b) providing a projection to be carried by the tab and to have a hook to engage a bone zone at its edge, and below said first level, c) and causing the projection to form a cantilever configuration which is resiliently deflected in a plane normal to the width dimension of the gap formed between the bone zone edge, by hook engagement with one of the bone zone edges.

An additional step may comprise fastening the tab to at least one of the bone zones.

Where two projections are employed, the method includes the steps a) providing a tab to extend over a surface or surfaces of at least one of said bone zones, above a level defined by the one surface, b) providing tab projections to be carried by the tab and to have hooks to engage a bone zone at its edge, and below said first level, c) and causing each projection to form a cantilever configuration which is resiliently deflected by hook engagement with one of said edges.

These and other objects and advantages of the invention, as well as the details of an illustrative embodiment, will be more fully understood from the following specification and drawings, in which:

DRAWING DESCRIPTION

FIG. 5 is a side elevation showing an improved clip, with a retention projection projected downwardly at an angle from the clip top plate or tab;

FIG. 6 is an end view taken on lines 6—6 of FIG. 5;

FIG. 7 is a bottom plan view taken on lines 7—7 of FIG. 5;

DETAILED DESCRIPTION

Figure 1:
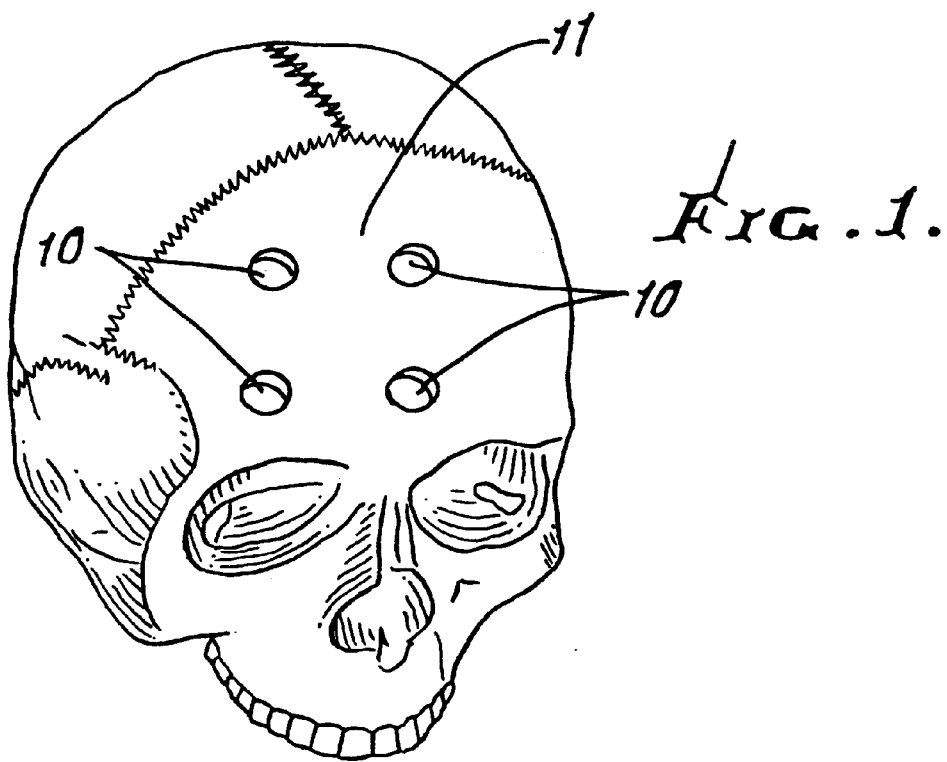
FIG. 1 is a view of a skull, showing drilled openings in the cranium arranged in a generally rectangular pattern.
Figure 2:
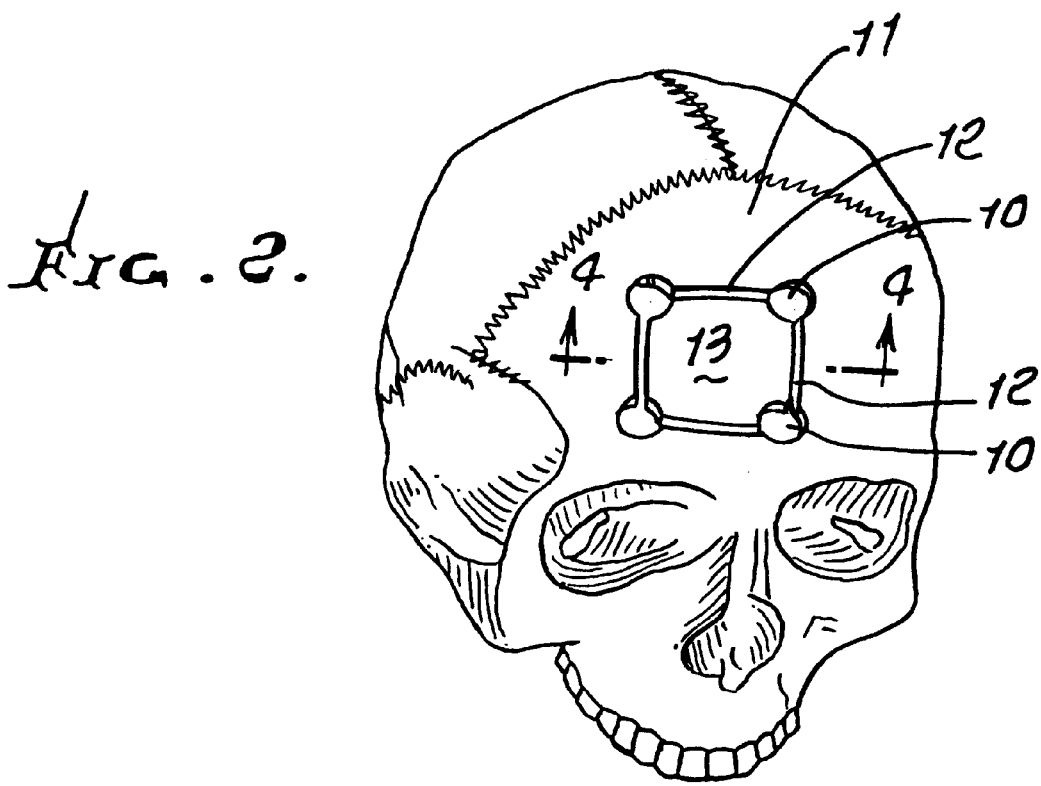
FIG. 2 is a fragmentary view showing slots formed between the FIG. 1 drilled openings.
Figure 3:
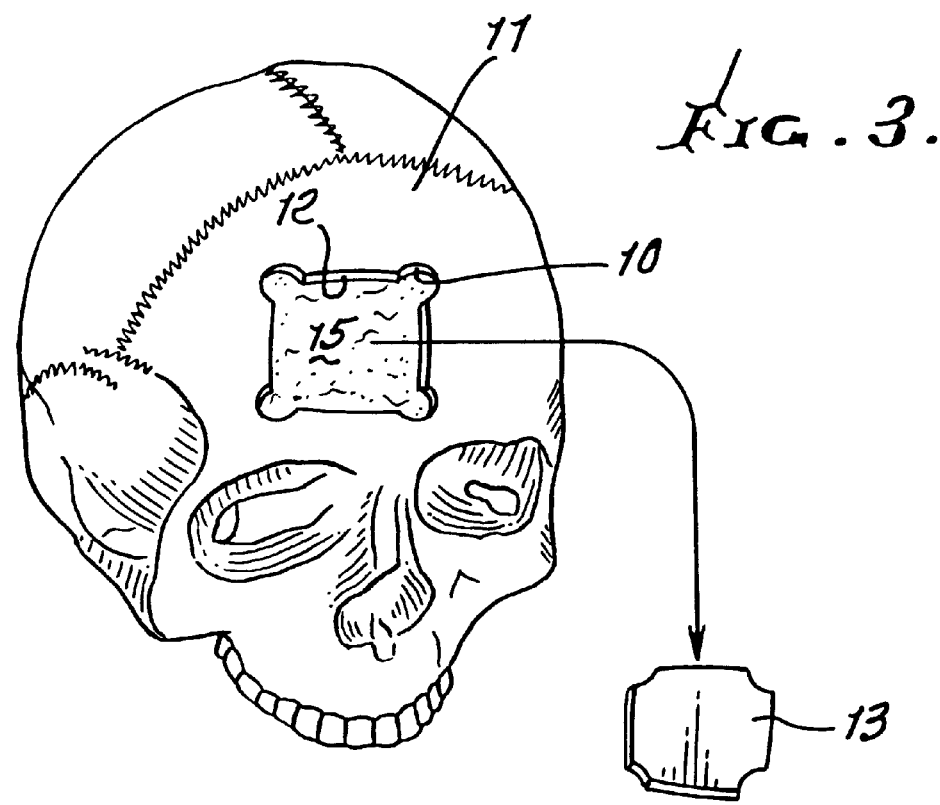
FIG. 3 is a fragmentary view showing a bone flap removed from the FIG. 2 skull cranium.

FIG. 1 shows the formation of holes 10 (for example four) in the cranium 11, as for example during brain surgery. FIG. 2 shows interconnection of the holes by cuts 12 in the cranium, to form the perimeter of a primary bone flap 13; and FIG. 3 shows removal at 14 of the flap, serving to expose the brain 15 for surgery.

Figure 4:
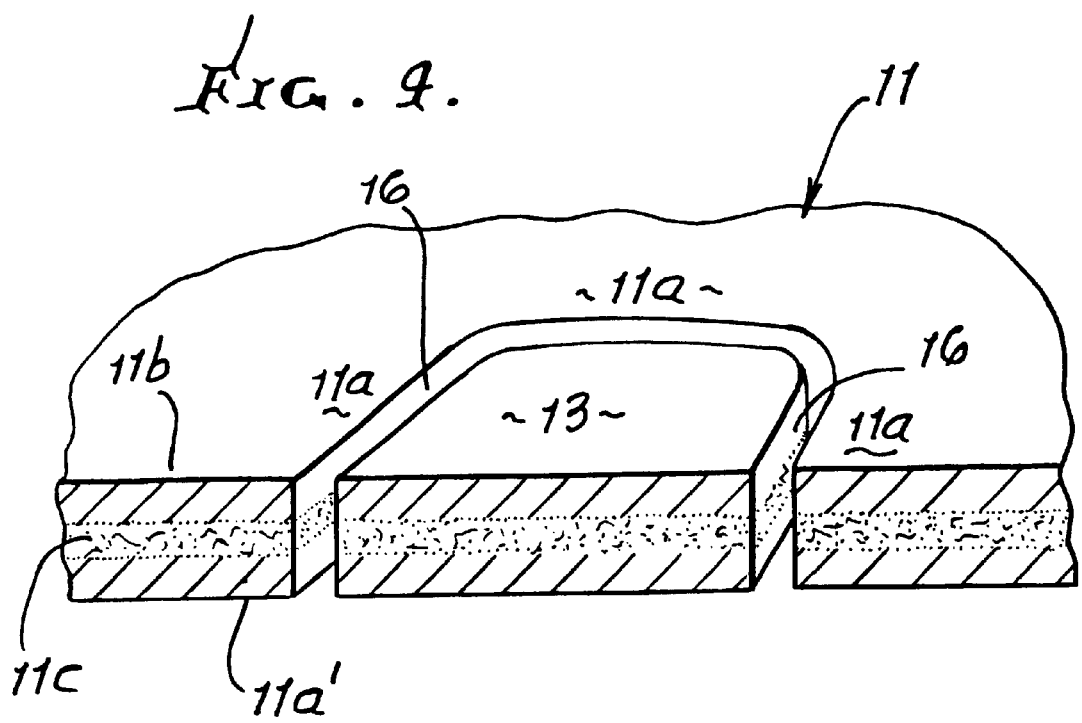
FIG. 4 is an enlarged perspective view taken in section, as on lines 4—4 of FIG. 2, to show the bone flap surrounded by a gap, in the cranium.
Figure 8:
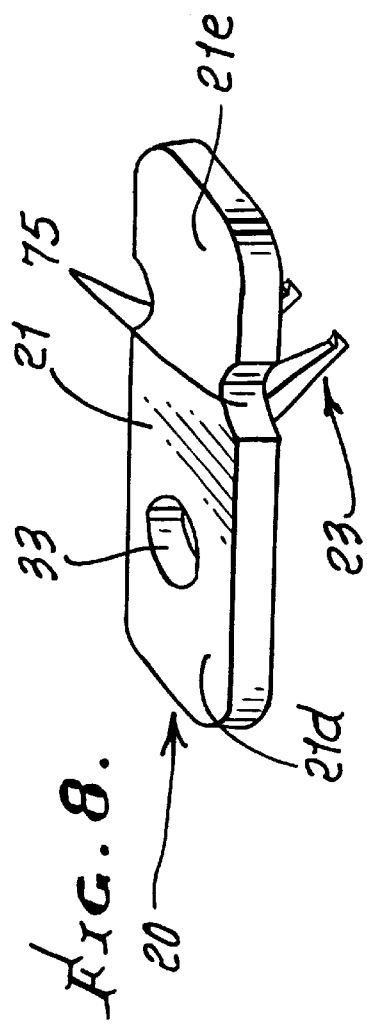
FIG. 8 is a perspective view of the FIG. 5 clip.

FIG. 4 shows, in perspective and enlarged section form, a gap 16 formed by cuts through the skull, the flap 13, and the skull secondary bone zone 11a extending adjacent the gap. Also depicted are inner and outer cortex portions 11a and 11b of the skull, and the medulary layer (soft bone and marrow) 11c between 11a and 11b, and used for flap retention purposes as will appear.

The clip seen at 20 in FIGS. 5–9, is employed to interconnect primary and secondary bone zones 11 and 13, proximate the gap 16 The clip includes:

a) a tab 21 such as a plate configured to extend over a surface such as at 22, or surfaces, of at least one of the bone zones, above a level 22a defined by that one surface, and b) a first projection as at 23 carried by the tab, and having a hook 23a to engage bone zone 11 at its edge and below said first level. See for example edge 11d of the skull, facing the gap 16, in FIG. 9.

The projection 23 typically extends angularly downwardly from the underside of the tab toward the hook, as for example at an angle α of between 50° and 60° relative to the plane 21a of tab 21, as seen in FIG. 5; and the hook 23a tapers in a direction 24, generally normal to the elongation direction 25 of the projection 23, whereby the sharp ended hook is well adapted to hook into the medulary layer 11c of the skull. Also, the projection 23 tapers in direction 25 toward the hook whereby its lower extent is more resilient, and it flexes (see FIG. 9) as the projection is displaced downwardly in gap 16, allowing the hook to accommodate to and gouge into exposed medulary layer, with force at least in part generated by such flexing. Note in FIG. 5 that the horizontal component of the unflexed hook length exceeds the width "w" of the gap.

Figure 9:
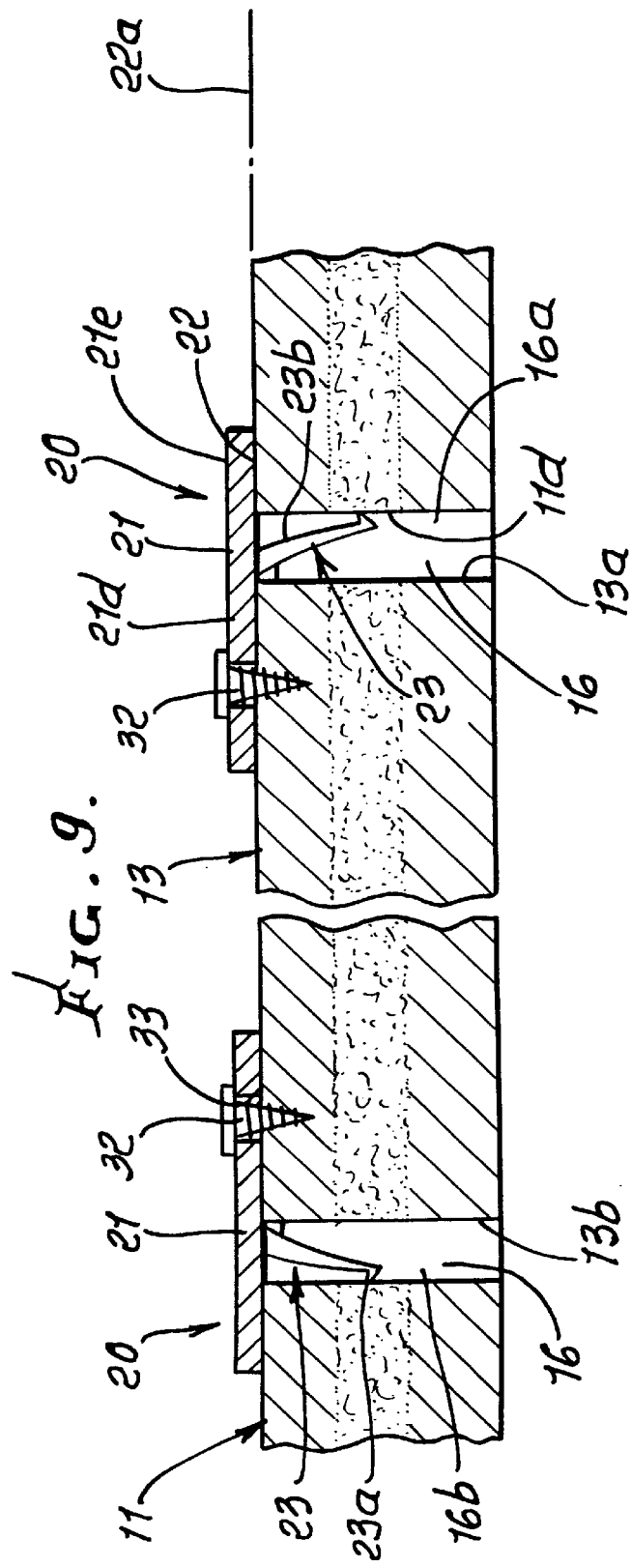
FIG. 9 is a section showing two FIG. 5 clips holding opposite ends of a bone flap to primary and secondary bone zones.

FIG. 9 shows how controlled flexing of two or more projections 23 is created, as they fit down into the gap 16 extents 16a and 16b at generally opposite ends 13a and 13b of the flap 13. The interference fit is such as to flex both projections 23, particularly at their lower narrower extents, as shown, whereby the gap extents 16a and 16b are kept approximately equal.

It will be noted that the projection 23 has a shank 23b that tapers toward the hook, the uppermost end of the projection being integral with the underside 21c of the tab 21, and at the side of the gap closest to the end or edge 13a of the flap 13. A spacer 30 is shown in FIGS. 5–7 protruding downwardly from the tab, to engage flap edge 13a, to locate the clip relative to the flap 13, at the time of clip attachment to the top surface of the flap. See for example the screw 32 in FIG. 9, projecting in hole 33 in the tab, and attaching it to the flap. Other means of attachment can be provided, one example being a bonding agent.

The tab 21 extends at 21d over the flap (for example the primary bone zone) and at 21e over the cranium nearest the gap (the secondary bone zone).

FIGS. 5–8 also show the provision of a second projection 123, like projection 23, but laterally spaced from 23. The two projections align themselves and bend relative to edge 11d, as they are installed so that hooks 23a and 123a engage that bone to best "bite effect".

Note the tapering opposite faces 23f and 23g of the projection 23 as seen in FIG. 5, and the tapering opposite edges 23h and 23i of the projection 23 as seen in FIGS. 6 and 7. Projection 123 is similarly bidirectionally tapered.

The method of clip attachment, includes a) providing a tab to extend over a surface or surfaces of at least one of said tab bone zones, above a level defined by the one surface, b) providing a projection formed to be carried by the tab and to have a hook to engage a bone zone at its edge, and below said first level, c) the projection formed to have a cantilever configuration which is resiliently deflected by hook engagement with one of said edges.

The method is also applicable to use of two projections 23 and 123.

Figure 10:
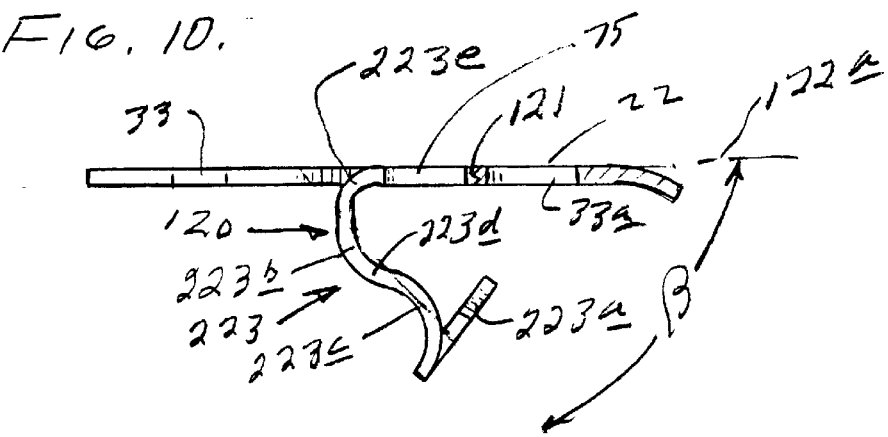
FIG. 10 is a side elevation showing a clip having a projection with S-configuration.

In FIG. 10, a modified clip 120 is used for the same purposes as clip 20 seen in FIGS. 5–9. The clip 120 includes:

a) a tab 121 such as a plate configured to extend over a surface such as surface 22 of at least one of the bone zones, above a first level 122a defined by that one surface, b) and a first projection as at 223 carried by the tab and having a hook 223a to engage bone zone 11 at its edge 11d facing gap 16 and below that first level, c) the projection being bowed, thereby enhancing the spring effect to engage and penetrate zone 11.

Figure 11:
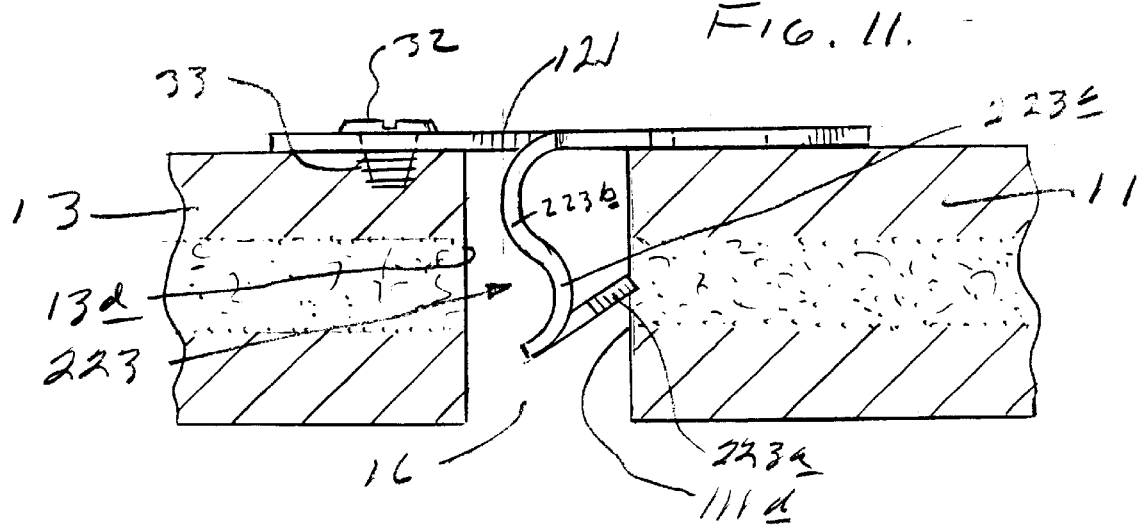
FIG. 11 is an elevation showing the FIG. 10 clip in installed condition.

The projection 223 typically may extend angularly downwardly from the tab underside, and at an angle β between about 50° and 60° relative to the plane of the tab 121; and the hook 123a tapers in a direction 124 away from a bowed lower section 223c of the projection. The latter is bowed in the direction of the hook, as shown; and the upper section 223b of the projection merges with the lower section at inflexion region 223d, and it also merges with the plate or tab at convex corner region 223e. Accordingly, the sharp ended hook is well adapted to hook into the medullary layer 11c of the skull. FIG. 11 shows this condition. The upper section 223b of the projection is bowed in the opposite direction, i.e. toward edge 13a of the gap, whereby the projection has increased bending stiffness, tending to urge the hook into the layer 11c of the skull. Edge 13a is formed on bone section 13, as shown.

Figure 12:
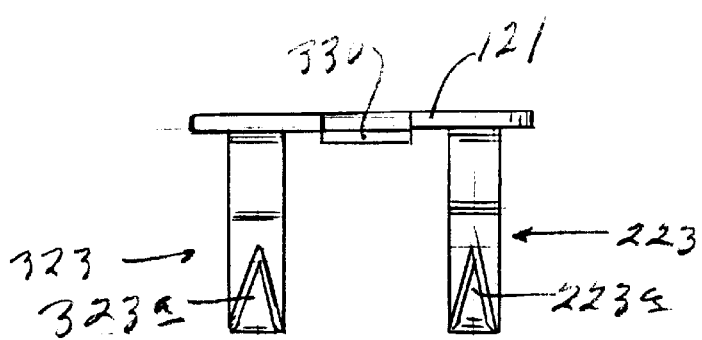
FIG. 12 is a front view of a clip like FIG. 10, but having two projections.

FIG. 12 shows provision of a second projection 323, like projection 223, but laterally spaced from 223. The two S-shaped projections align themselves and bend, relative to edge 11a, as they are installed, so that hooks 223a and 323a engage that bone to best "bite effect", while allowing the gap width to adjust during installation, as described above. An alignment protrusion appears at 330 and corresponds to protrusion 30 seen in FIGS. 6 and 7.

The method of clip attachment includes a) providing a tab to extend over a surface or surfaces of at least one of the bone zones, above a level defined by that surface, b) providing a projection to be carried by the tab and to have a hook to engage a bone zone at its edge, and below said level, c) the projection formed to have a cantilever configuration which is resiliently deflected by hook engagement with the bone zone edge, d) the projection also formed to have bowed configuration.

In the above, the metallic clip may advantageously consist essentially of one of the following:
  i) titanium
  ii) titanium alloy
  iii) titanium-aluminum-vanadium alloy
  iv) an alloy consisting essentially of:
    about 90% by weight of titanium
    about 6% by weight of aluminum
    about 4% by weight of vanadium.

Fastener holes in the tab appear at 33 and 33a.

We claim:

1. A clip to inter-connect primary and secondary bone zones having edges, comprising in combination:
   a) a tab to extend over at least one surface or surfaces of at least one of said bone zones, above a level defined by the one surface, and
   b) a first projection carried by the tab and having a hook to engage a bone zone at its edge, and below a portion of the tab that extends over the projection,
   c) the projection being bowed,
   d) the hook having an underside that is inclined upwardly toward a plane defined by the tab.

2. The combination of claim 1 wherein the projection has sections at least one of which is bowed.

3. The combination of claim 2 wherein the section defines an S-configuration.

4. The combination of claim 2 wherein said hook is carried by said one bowed section.

5. The combination of claim 4 wherein said hook projects away from said one bowed section, which is bowed toward the direction of hook projection.

6. The combination of claim 1 wherein another of said sections is integral with the tab.

7. The combination of claim 1 wherein said hook has a sharp terminal angled to enable penetration of bone marrow.

8. The combination of claim 1 including a through hole in the tab to receive a fastener that fastens to one of said bone zones.

9. The combination of claim 1 wherein the tab is elongated to bridge portions of both the primary and secondary bone zones.

10. The combination of claim 1 wherein said primary bone zone is configured to have an outline corresponding to a cranial bone flap.

11. The combination of claim 1 including a second projection carried by the tab and having a hook to engage the said one bone zone at its edge, and below said level, said second projection also being bowed.

12. The combination of claim 11 wherein said first and second projections extend in generally parallel relation, and downwardly to terminate at said hooks.

13. The combination of claim 12 including said primary and secondary bone zones defining a gap between edges thereof, each projection defining a cantilever configuration which is resiliently deflected by hook engagement with at least one of said edges.

14. The combination of claim 13 wherein one of said bone zones is a bone flap removed from a cranium.

15. The combination of claim 1 wherein said primary and secondary bone zones define a gap between edges thereof, said projection defining a cantilever configuration which in use is resiliently deflected by hook engagement with one of said edges.

16. The combination of claim 15 wherein one of said bone zones is a bone flap removed form a cranium.

17. A clip to inter-connect primary and secondary bone zones having edges, comprising in combination:
   a) a tab to extend over at least one surface or surfaces of at least one of said bone zones, above a level defined by the one surface, and
   b) a first projection carried by the tab and having a hook to engage a bone zone at its edge, and below a portion of the tab that extends over the projection,
   c) the projection being bowed,
   d) and wherein the tab has at least one retraction notch proximate the end of the first projection closest to the tab.

18. A clip to inter-connect primary and secondary bone zones having edges, comprising in combination:
   a) a tab to extend over at least one surface or surfaces of at least one of said bone zones, above a level defined by the one surface, and
   b) a first projection carried by the tab and having a hook to engage a bone zone at its edge, and below a portion of the tab that extends over the projection
   c) the projection being bowed,
   d) a through hole in the tab to receive a fastener that fastens to one of said bone zones,
   e) and wherein the tab has retraction notches proximate the ends of said projections closest to the tab.

19. A clip to inter-connect primary and secondary bone zones having edges, comprising in combination:
   a) a tab to extend over at least one surface or surfaces of at least one of said bone zones, above a level defined by the one surface, and
   b) a first projection carried by the tab and having a hook to engage a bone zone at its edge, and below a portion of the tab that extends over the projection
   c) the projection being bowed,
   d) a second projection carried by the tab and having a hook to engage the said one bone zone at its edge, and below said level, said second projection also being bowed,
   e) said first and second projections extending in generally parallel relation, and downwardly to terminate at said hooks,
   f) and including an alignment protrusion integral with the tab, and located between the first and second projections for engagement with an edge of the primary bone zone.

20. The method of clip attaching primary and secondary body zones having edges, that include:
   a) providing a tab to extend over a surface or surfaces of at least one of said bone zones, above a level defined by the one surface,
   b) providing a projection to be carried by the tab and to have a hook to engage a bone zone at its edge, and below said level,
   c) the projection formed to have a cantilever configuration which is resiliently deflected by hook engagement with one of said edges,
   d) said projection also formed to have bowed configuration.

21. The method of claim 20 including providing said projection to have sections one of which is bowed, and locating said hook on said one bowed section.

22. A clip to interconnect primary and secondary bone zones having edges, comprising in combination:
   a) a tab to extend over a surface or surfaces of at least one of said bone zones, above a level defined by the one surface, and
   b) a first projection carried by the tab and having a hook to engage a bone zone at its edge, and below a portion of said tab that extends over the projection,
   c) said projection extending angularly downwardly along its length and away from the tab at an angle between about 50° and 60° from a plane defined by the tab, and terminating at said hook,
   d) the hook projecting sidewardly of the projection, at the end thereof,
   e) said projection and hook both everywhere located beneath the tab,
   f) the hook having an underside that tapers upwardly toward a plane defined by the tab.

23. The combination of claim 22 wherein the clip consists essentially of one of the following:
   i) titanium
   ii) titanium alloy
   iii) titanium-aluminum-vanadium alloy
   iv) an alloy consisting essentially of:
      about 90% by weight of titanium
      about 6% by weight of aluminum
      about 4% by weight of vanadium.

* * * * *